US00PP26921P3

(12) United States Plant Patent

Nelson et al.

(10) Patent No.: US PP26,921 P3

(45) Date of Patent: Jul. 12, 2016

(54) STRAWBERRY PLANT NAMED 'BG-4.352'

(50) Latin Name: *Fragaria ananassa*
Varietal Denomination: BG-4.352

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 109 days.

(21) Appl. No.: 14/121,353

(22) Filed: Aug. 25, 2014

(65) Prior Publication Data

US 2016/0057903 P1 Feb. 25, 2016

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para

(74) *Attorney, Agent, or Firm* — Foley & Lardner LLP

(57) ABSTRACT

This invention relates to a new and distinct variety of strawberry plant named 'BG-4.352'. This new strawberry plant named 'BG-4.352' is primarily adapted to the growing conditions of the central coast of California, and is primarily characterized by its orange red to red fruit color, large fruit size, many seeds per berry, very early fruit production, small foliage, and heavy pubescence on the petioles and fruiting trusses.

4 Drawing Sheets

BACKGROUND OF THE INVENTION

The present invention relates to a new and distinct strawberry variety named 'BG-4.352'. This new variety is a result of a controlled cross made in 2004 in an ongoing breeding program between strawberry variety designated 'PS-1269' (U.S. Plant Pat. No. 10,686) and strawberry variety designated 'BG-414.065' (a non-patented selection). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the winter of 2006. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-4.352' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-4.352', which in combination distinguish this strawberry plant as a new and distinct variety:

1. Orange red to red fruit color;
2. Large fruit size;
3. Many seeds per berry;
4. Very early fruit production;
5. Small foliage; and
6. Heavy pubescence on the petioles and fruiting trusses.

The strawberry variety that is believed to be most closely related to the new variety 'BG-4.352' is 'BG-959' (U.S. Plant Pat. No. 17,864). In side-by-side comparisons to the similar strawberry variety 'BG-959', 'BG-4.352' differs by the following combination of characteristics as described in Table 1.

TABLE 1

| Characteristic | 'BG-4.352' | 'BG-959' (U.S. Plant Pat. No. 17,864) |
|---|---|---|
| Fruit: color | Ranges from orange red to red | Red |
| Fruit: size (grams) | 30.7 (large) | 27.2 (medium) |
| Fruit: predominant shape | Ranges from conical to cylindrical | Conical |
| Fruit: insertion of achenes | Ranges from level with to below the surface | Level with the surface |
| Time of first fruit production | Very early | Early |
| Plant: size | Medium | Ranges from medium to small |
| Foliage: color | Medium yellow green | Ranges from medium to dark green |
| Fruiting truss: position relative to foliage | Ranges from level with to above | Level with |
| Fruiting truss: pubescence | Strong | Medium |

For identification, a series of molecular markers have been determined for this new variety.

'BG-4.352' differs from its parents, 'PS-1269' and 'BG-414.065' by the following combination of characteristics as described in Table 2.

TABLE 2

| Characteristic | 'BG-4.352' | 'PS-1269' (U.S. Plant Pat. No. 10,686) | 'BG-414.065' |
|---|---|---|---|
| Type of bearing | Not remontant (short day) | Partially remontant (summer bearing) | Not remontant (short day) |
| Fruit size | Large | Medium | Small |
| Plant size | Medium | Ranges from medium to large | Large |
| Fruit color | Ranges from orange red to red | Red | Red |

BRIEF DESCRIPTIONS OF THE PHOTOGRAPHS

The accompanying color photographs illustrate the overall appearance of typical specimens of the new strawberry variety 'BG-4.352' at various stages of development, as true as it is reasonably possible with color reproductions of this type. Color in the photographs may differ slightly from the color value cited in the botanical descriptions which accurately describe the color of 'BG-4.352'. The depicted plant and plant parts of the new strawberry variety 'BG-4.352' are approximately five to six months old. The photographs were taken in Ventura County, Calif.

DETAILED BOTANICAL DESCRIPTION

Figure 1:
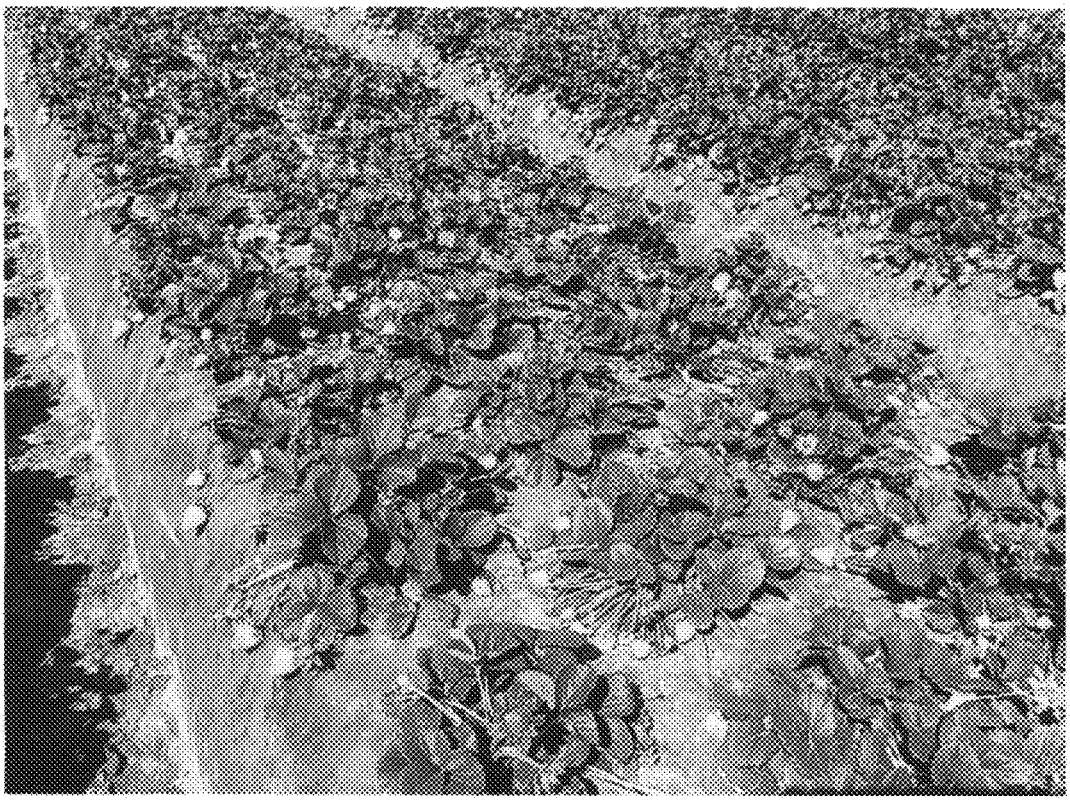
FIG. 1 shows typical fruiting field characteristics of 'BG-4.352', taken in the month of April 2014.
Figure 2:
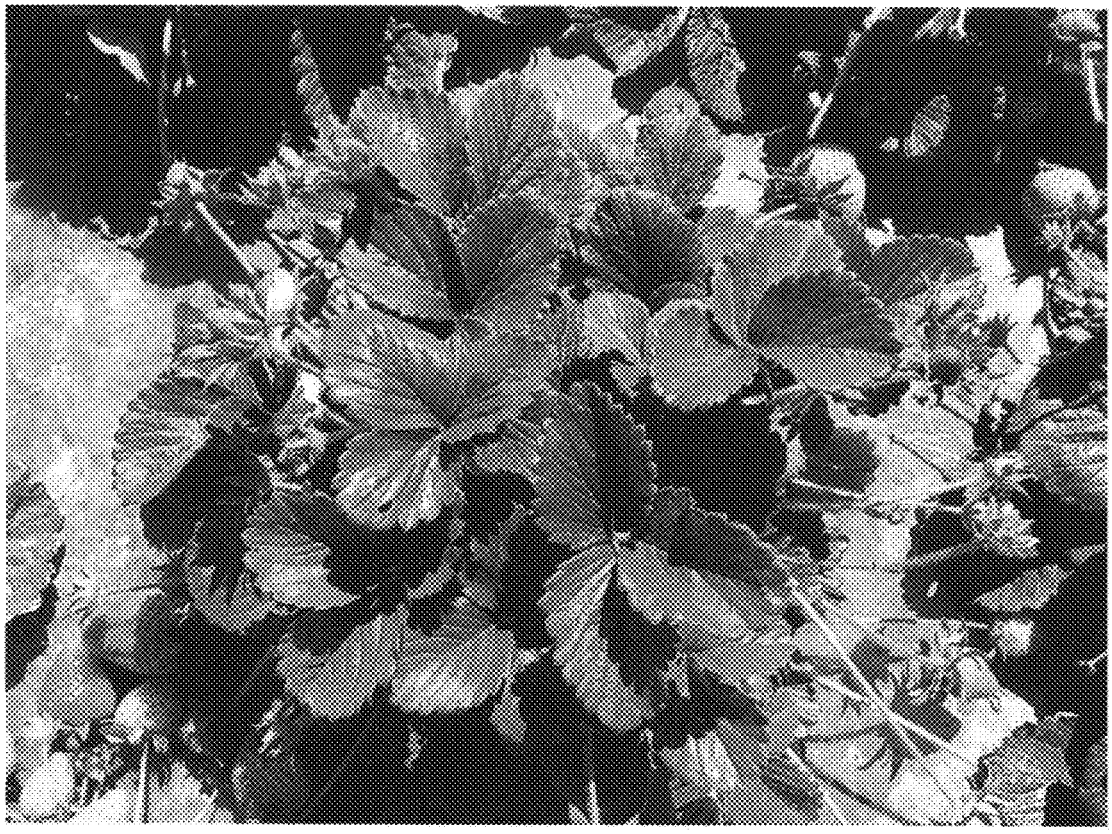
FIG. 2 shows a close-up view of the typical leaf structure of 'BG-4.352', taken in the month of April 2014.
Figure 3:
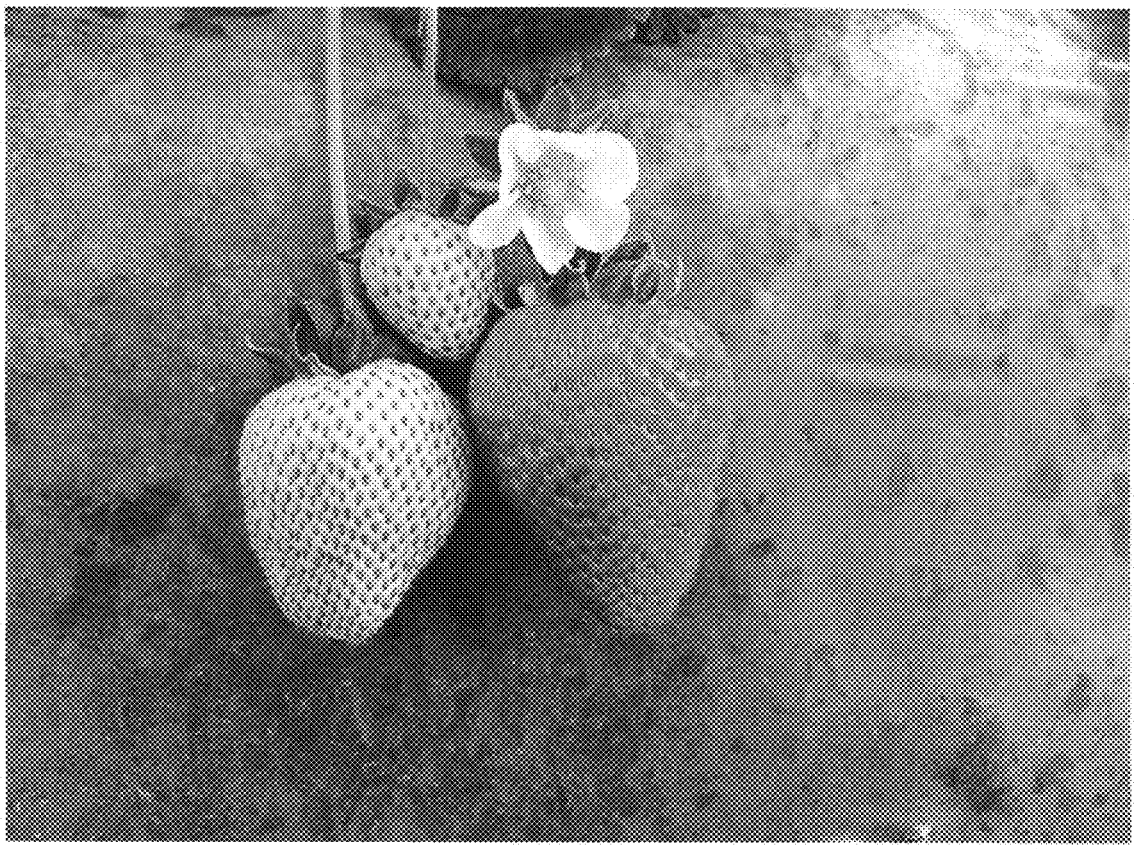
FIG. 3 shows typical mature and immature field fruit of 'BG-4.352', taken in the month of March 2014.
Figure 4:
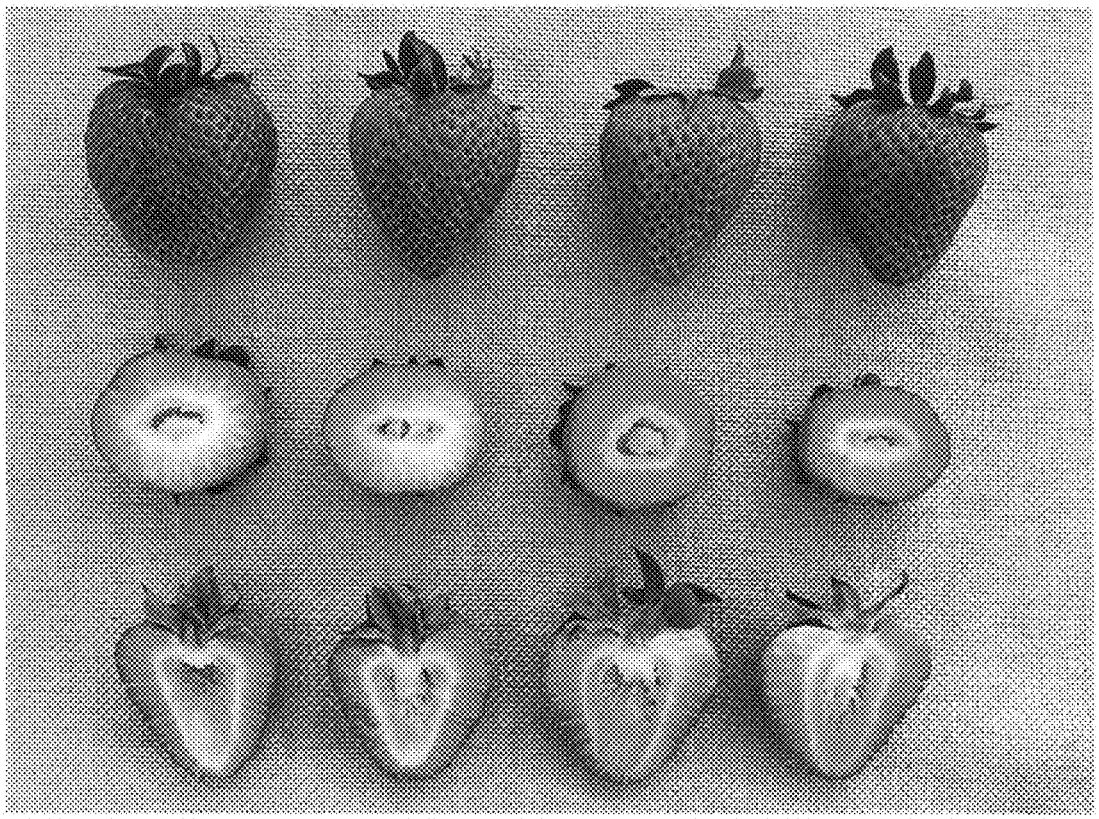
FIG. 4 shows typical internal and external mature fruit characteristics of 'BG-4.352', taken in the month of March 2014.

The new variety 'BG-4.352' has not been observed under all possible environmental conditions. The characteristics of the new variety 'BG-4.352' may vary in detail, depending upon variations in environmental factors, including weather (temperature, humidity and light intensity), day length, soil type and location. In addition, the characteristics of any parental variety or comparison variety included in Tables 3 through 9 of the present invention may vary in detail, depending upon variations in environmental factors, including weather (temperature, humidity and light intensity), day length, soil type and location.

The aforementioned photographs, together with the following description of the new variety 'BG-4.352', unless otherwise noted, are based on observations taken during the 2014 growing season in Ventura County, Calif. These measurements and ratings were taken from plants of 'BG-4.352' dug from a high-elevation nursery located in Siskiyou County, Calif. during early October 2013 and planted approximately four to five days later in Ventura County, Calif. The approximate age of the observed plants is five to six months. Yield observations and fruit quality characteristics are averaged from five years of data collected from the 2010 through 2014 growing seasons. Flower measurements and characteristics are from secondary flowers unless otherwise noted. Fruit characteristics and measurements are from secondary fruit, unless otherwise noted.

Color terminology where noted follows The Royal Horticultural Society Colour Chart, London (2007).

The following Tables 3 through 9 describe fruit, plant, stolon, foliage, fruiting truss, flower, and pest and disease characteristics of the new strawberry 'BG-4.352'.

TABLE 3

FRUIT CHARACTERISTICS

| Characteristic | 'BG-4.352' |
|---|---|
| Color of mature fruit | RHS 45A, ranges from orange red to red |
| Color of internal flesh | RHS 45B, medium red |
| Color of core | RHS 39A, medium red |
| Fruit length (cm) | 4.7 |
| Fruit width (cm) | 3.9 |
| Fruit size | Large |
| Fruit length/width ratio | 1.20, ranges from slightly longer than broad to much longer than broad |
| Calyx diameter (cm) | 4.1 |
| Average fruit weight (gm) | 30.7 |
| Achene color, shaded side | RHS 153B, yellow green group |
| Achene color, sun-exposed side | RHS 182A, greyed red group |
| Achene weight (mg) | 0.42 |
| Average achenes per berry | 583 |
| Marketable fruit yield (gm/plant) | 1,096 |
| Predominant fruit shape | Ranges from conical to cylindrical |
| Difference in shapes between primary and secondary fruit | Slight |
| Band without achenes | Absent or very narrow |
| Evenness of fruit surface | Even or very slightly uneven |
| Evenness of fruit color | Even or very slightly uneven |
| Fruit glossiness | Medium |
| Insertion of achenes | Ranges from below surface to level with surface |
| Position of calyx attachment | Inserted |
| Attitude of sepals | Outward |
| Size of calyx relative to fruit diameter | Same size |
| Adherence of calyx (when fully ripe) | Strong |
| Firmness of fruit flesh | Ranges from medium to firm |
| Distribution of red color of the flesh | Marginal and central |
| Hollow center expression | Moderate |
| Fruit flavor | Good |
| Soluble solids (% Brix) | 6.7 |
| Time of first flower | Very early |
| Time of first harvest | Very early |
| Harvest period | January to June |
| Harvest maturity | Early season |
| Type of bearing | Not remontant (short day) |

TABLE 4

PLANT CHARACTERISTICS

| Characteristic | 'BG-4.352' |
|---|---|
| Plant height (cm) | 15.1 |
| Plant spread (cm) | 30.8 |
| Plant size | Medium |
| Plant habit | Semi-upright |
| Plant density | Medium |
| Plant vigor | Medium |

TABLE 5

| STOLON CHARACTERISTICS | |
|---|---|
| Characteristic | 'BG-4.352' |
| Stolon color | RHS 146D, yellow green group |
| Stolon anthocyanin coloration | RHS 180C, greyed red group |
| Stolon anthocyanin intensity | Medium |
| Stolon pubescence | Dense |
| Attitude of hairs | Slightly outward |
| Average stolon quantity | Medium |
| Average stolon diameter at bract (mm) | 3.4 |

TABLE 6

| FOLIAGE CHARACTERISTICS | |
|---|---|
| Characteristic | 'BG-4.352' |
| Foliage: | |
| Color of upper surface | RHS 146A, medium yellow green |
| Color of underside | RHS 138B, green group |
| Number of leaflets | 3 |
| Shape in cross section | Ranges from slightly concave to slightly convex |
| Interveinal blistering | Medium |
| Leaf glossiness | Medium |
| Leaf variegation | Absent |
| Terminal Leaflet: | |
| Length (cm) | 5.6 |
| Width (cm) | 5.1 |
| Leaf size | Small |
| Length/width ratio | 1.09, longer than broad |
| Shape of base | Obtuse |
| Margins (shape of teeth) | Rounded (crenate) |
| Serrations per leaf | 20.7 |
| Petiole: | |
| Petiole color | RHS 144B, yellow green group |
| Petiole length (cm) | 8.7 |
| Petiole diameter (mm) | 2.8 |
| Petiolule color | RHS 144B, yellow green group |
| Petiolule length (mm) | 7.8 |
| Attitude of hairs | Strongly outward |
| Petiole pubescence | Ranges from heavy to moderate |
| Stipule: | |
| Color | RHS 146B, yellow green group |
| Anthocyanin coloration | RHS 58A, red purple group |
| Anthocyanin intensity | Medium |
| Length (mm) | 16.4 |
| Width (mm) | 10.8 |

TABLE 7

| FRUITING TRUSS CHARACTERISTICS | |
|---|---|
| Characteristic | 'BG-4.352' |
| Anthocyanin coloration | RHS 182C, greyed red group |
| Anthocyanin intensity | Medium |
| Length at maturity (cm) | 21.2 |
| Position relative to foliage | Ranges from level with to above |
| Number of flowers | Medium |
| Pedicel attitude of hairs | Strongly outward |
| Pubescence | Strong |
| Attitude at first pick | Prostrate |

TABLE 8

| FLOWER CHARACTERISTICS | |
|---|---|
| Characteristic | 'BG-4.352' |
| Petal color | RHS NN155C, white group |
| Sepal color | RHS 137A, green group |
| Receptacle color | RHS 147C, yellow green group |
| Anther color | RHS 13A, yellow group |
| Corolla diameter (mm) | 29.6, medium |
| Calyx diameter (mm) | 32.4 |
| Petal length (mm) | 9.7 |
| Petal width (mm) | 10.3 |
| Petal length/width ratio | 0.95, broader than long |
| Petals per flower | 6.0 |
| Sepal length (mm) | 10.6 |
| Sepal width (mm) | 4.7 |
| Sepal length/width ratio | 2.26 |
| Sepals per flower | 11.6 |
| Size of calyx relative to corolla | Larger |
| Relative position of petals | Overlapping |
| Stamen | Present |
| Size of inner calyx relative to outer calyx | Ranges from smaller to same |

TABLE 9

| PEST AND DISEASE REACTIONS | |
|---|---|
| Characteristic | 'BG-4.352' |
| Powdery mildew | Moderately susceptible |
| Verticillium wilt | Moderately susceptible |
| Angular leaf spot | Susceptible |
| Botrytis fruit rot | Moderately susceptible |
| Two-spotted spider mite | Moderately susceptible |

We claim:

1. A new and distinct strawberry plant named 'BG-4.352', as herein described and illustrated by the characteristics set forth above.

* * * * *